(12) United States Patent
Sawant et al.

(10) Patent No.: US 7,671,145 B2
(45) Date of Patent: Mar. 2, 2010

(54) EPOXY-CAPPED POLYTHIOETHERS BY REACTING DITHIOL, DIOLEFIN AND MONOEPOXY OLEFIN

(75) Inventors: Suresh Sawant, Stevenson Ranch, CA (US); Chandra Bhushan Rao, Valencia, CA (US)

(73) Assignee: PRC DeSoto International, Inc., Glendale, CA (US)

( * ) Notice: Subject to any disclaimer, the term of this patent is extended or adjusted under 35 U.S.C. 154(b) by 461 days.

(21) Appl. No.: 11/369,490

(22) Filed: Mar. 7, 2006

(65) Prior Publication Data

US 2007/0299217 A1    Dec. 27, 2007

Related U.S. Application Data

(63) Continuation of application No. 10/617,582, filed on Jul. 11, 2003, now abandoned.

(51) Int. Cl.
    *C08G 59/02*    (2006.01)
(52) U.S. Cl. ............................... 525/523; 528/376
(58) Field of Classification Search ............. None
    See application file for complete search history.

(56) References Cited

U.S. PATENT DOCUMENTS

| | | | | |
|---|---|---|---|---|
| 6,372,849 | B2 * | 4/2002 | DeMoss et al. | 525/212 |
| 6,800,371 | B2 * | 10/2004 | Schultz et al. | 428/413 |
| 7,097,883 | B2 * | 8/2006 | Sawant et al. | 427/385.5 |
| 2005/0010003 | A1 * | 1/2005 | Sawant et al. | 525/523 |
| 2007/0287810 | A1 * | 12/2007 | Rao et al. | 525/523 |

* cited by examiner

*Primary Examiner*—Robert Sellers
(74) *Attorney, Agent, or Firm*—Diane R. Meyers

(57) ABSTRACT

Epoxy-capped polythioethers and curable compositions of epoxy-capped polythioethers are disclosed.

17 Claims, No Drawings

EPOXY-CAPPED POLYTHIOETHERS BY REACTING DITHIOL, DIOLEFIN AND MONOEPOXY OLEFIN

CROSS-REFERENCE TO RELATED APPLICATIONS

This application is a continuation of U.S. patent application Ser. No. 10/617,582 filed Jul. 11, 2003, entitled: Epoxy-capped Polythioethers", now abandoned.

FIELD OF THE INVENTION

This invention generally relates to epoxy-capped polythioethers and curable compositions of epoxy-capped polythioethers.

BACKGROUND OF INVENTION

It is desirable that sealants, coatings, and adhesives used in aviation and aerospace applications exhibit flexibility, fuel resistance, and high-temperature resistance. In general, these properties may be accomplished by incorporating polythioether linkages into the backbone of polymer resins.

Flexible, fuel resistant epoxy-terminated polysulfides have been developed which exhibit good fuel resistance. These compounds are typically formed using epichlorohydrin as a reactant. Epichlorohydrin is extremely toxic and the synthesis of epoxy-terminated polysulfides using epichlorohydrin generates corrosive hydrolysable chlorine ("HYC") as an undesirable byproduct. Further, the compounds formed using epichlorohydrin incorporate un-reacted epichlorohydrin that must be removed by thorough washing. Such epoxy-terminated polysulfides typically exhibit a relatively high viscosity of about 30 poise at 25° C. and a broad epoxy equivalent weight range.

There is a need for improved flexible, fuel resistant, and high-temperature resistant epoxy-capped polythioethers and compositions of epoxy-capped polythioethers synthesized by methods that are environmentally compatible and that do not produce toxic byproducts. Further, it is desirable to produce epoxy-capped polythioethers with a controlled and narrow epoxy equivalent weight range.

The epoxy-capped polythioethers of the invention formed by the addition of thiol across the double bond of a monoepoxide comprising an olefinic group are flexible, fuel resistant and the high-conversion synthesis does not generate hydrolysable chlorine and avoids the use of epichlorohydrin. The epoxy capped polythioethers of the invention exhibit a controlled and narrow epoxy-equivalent weight distribution.

SUMMARY OF THE INVENTION

To address the limitations of known epoxides for aviation and aerospace application there is provided epoxy-capped polythioethers and curable compositions of epoxy-capped polythioethers.

One aspect of the invention provides epoxy-capped polythioethers having the structure of Formula I:

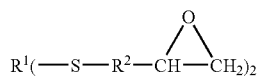

I wherein
R$^1$ is selected from the group consisting of C$_{2-6}$ n-alkylene, C$_{3-6}$ branched alkylene, C$_{6-8}$ cycloalkylene, C$_{6-10}$ alkylcycloalkylene, —[—(CHR$^3$)$_p$—X—]$_q$—(CHR$^3$)$_r$—,
wherein
each R$^3$ is independently selected from H, and CH$_3$,
each X is independently selected from O, S, —NH—, and —NR$^4$—,
R$^4$ is selected from H, and —CH$_3$,
p is an integer from 2 to 6,
q is an integer from 1 to 5, and
r is an integer from 2 to 10,
and each R$^2$ is a divalent linking group.

A second aspect of the invention provides epoxy-capped polythioethers formed by reacting n moles of a compound having the structure of Formula II wherein R$^1$ has the meaning described above:

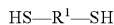

HS—R$^1$—SH    II with n+1 moles of a compound having the structure of Formula III wherein R$^2$ forms a divalent liking group:

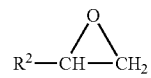

III

A third aspect of the invention provides curable compositions of the epoxy-capped polythioethers of the invention.

It is to be understood that both the foregoing general description and the following detailed description are exemplary and explanatory only and are not restrictive of the invention, as claimed.

DETAILED DESCRIPTION

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Consistent with the invention, one embodiment provides epoxy-capped polythioethers having the structure of Formula I:

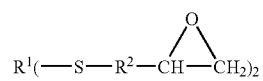

I wherein
R$^1$ is selected from the group consisting of C$_{2-6}$ n-alkylene, C$_{3-6}$ branched alkylene, C$_{6-8}$ cycloalkylene, C$_{6-10}$ alkylcycloalkylene, —[—(CHR$^3$)$_p$—X—]$_q$—(CHR$^3$)$_r$—,
wherein
each R$^3$ is independently selected from H, and CH$_3$, each X is independently selected from O, S, —NH—, and —NR$^4$—, R$^4$ is selected from H, and —CH$_3$, p is an integer from 2 to 6, q is an integer from 1 to 5, and r is an integer from 2 to 10, and each R$^2$ is a divalent linking group, typically alkylene or oxyalkylene containing from 3 to 20 carbon atoms.

R$^1$ is typically derived from compounds, monomers, or polymers having at least two thiol groups. In certain embodiments, polythiols include dithiols having the structure of Formula II:

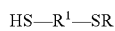     II where R$^1$ can be a C$_{2-6}$ n-alkylene group; a C$_{3-6}$ branched alkylene group having one or more pendent groups which can be, for example, hydroxyl groups, and alkyl groups such as methyl or ethyl groups; an alkyleneoxy group; a C$_{6-8}$ cycloalkylene group; a C$_{6-10}$ alkylcycloalkylene group; or a —[(—CHR$^3$)$_p$—X—]$_q$—(—CHR$^3$)$_r$— group, p is an independently selected integer ranging from 2 to 6, q is an independently selected integer ranging from 1 to 5, and r is an independently selected integer ranging from 2 to 10, and R$^3$ is hydrogen or methyl.

In other embodiments, dithiols may include one or more heteroatom substituents in the carbon backbone, that is, dithiols in which X includes a heteroatom such as O, S, or other bivalent heteroatom radical; a secondary or tertiary amine group, i.e., —NR$^4$—, where R$^4$ may be hydrogen or methyl; or other substituted trivalent heteroatom. In certain embodiments, X may be O or S, and thus R$^1$ is —[(—CHR$^3$)$_p$—O—]$_q$—(—CHR$^3$)$_r$—, or —[(CHR$^3$)$_p$—S—]$_q$—(—CHR$^3$)$_r$—. In certain embodiments, p and r are equal. In certain embodiments, both p and r have the value of 2.

In certain embodiments, the dithiols may include dimercaptodiethylsulfide (DMDS) (p=2, r=2, q=1, X=S), dimercaptodioxaoctane (DMDO) (p=2, q=2, r=1, X=O), and 1,5-dimercapto-3-oxapentane (p=2, r=2, q=1, X=O). In certain embodiments, the dithiols may include both heteroatom substituents in the carbon backbone and pendent alkyl groups, such as pendent methyl groups. Examples of dithiols having both heteroatom substituents in the carbon backbone and pendent alkyl groups include methyl-substituted DMDS such as HS—CH$_2$CH(CH$_3$)—S—CH$_2$CH$_2$—SH, and HS—CH(CH$_3$)CH$_2$—S—CH$_2$CH$_2$—SH, and dimethyl-substituted DMDS such as HS—CH$_2$CH(CH$_3$)—S—CH(CH$_3$)CH$_2$—SH and HS—CH(CH$_3$)CH$_2$—S—CH$_2$CH(CH$_3$)—SH.

In certain embodiments of epoxy-capped polythioethers having the structure of Formula I, R$^1$ may be a C$_{2-6}$ n-alkylene group, for example, 1,2-ethylenedithiol, 1,3-propylenedithiol, 1,4-butylenedithiol, 1,5-pentylenedithiol, or 1,6-hexylenedithiol. In other embodiments, R$^1$ may be a C$_{3-6}$ branched alkylene group having one or more pendent groups, for example, 1,2-propylenedithiol, 1,3-butylenedithiol, 2,3-butylenedithiol, 1,3-pentylenedithiol, and 1,3-dithio-3-methylbutylene. In other embodiments, R$^1$ may be a C$_{6-8}$ cycloalkylene or C$_{6-10}$ alkylcycloalkylene group, for example, dipentylenedimercaptan, and ethylcyclohexylenedithiol (ECHDT).

Polythiols having the structure of Formula II may be prepared by reacting, for example, a divinyl ether or mixture of divinyl ethers with an excess of a dithiol or a mixture of dithiols. In certain embodiments, n+1 moles of a polythiol having the structure of Formula II or a mixture of at least two polythiols having the structure of Formula II are reacted with n moles of a polyvinyl ether having the structure of Formula IV:

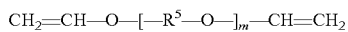     IV where R$^5$ includes a C$_{2-6}$ n-alkylene group, a C$_{3-6}$ branched alkylene group, a C$_{6-8}$ cycloalkylene group, a C$_{6-10}$ alkylcycloalkylene group, and a —[—(CHR$^3$)$_p$—X—]$_q$—(CHR$^3$)$_r$—, group where X, R$^3$, p, q, and r may be as set forth above, and m can be a rational number from 1 to 10.

Polyvinyl ethers can comprise compounds having at least one alkleneoxy group, and preferably from 1 to 4 alkyleneoxy groups, such as compounds in which m is an integer from 1 to 4. In other embodiments, m is an integer from 2 to 4. In certain embodiments, the polyvinyl ethers comprise polyvinyl ether mixtures. Such mixtures are characterized by a non-integral average value of the number of alkyleneoxy groups per molecule. Thus, m in Formula IV can also take on rational number values between 0 and 10.0, in other embodiments between 1.0 and 10.0, in still other embodiments between 1.0 and 4.0, and in still other embodiments between 2.0 and 4.0.

Polyvinyl ether monomers can comprise divinyl ether monomers, such as divinyl ether, ethylene glycol divinyl ether (EG-DVE), butanediol divinyl ether (BD-DVE), hexanediol divinyl ether (HD-DVE), diethylene glycol divinyl ether (DEG-DVE), triethylene glycol divinyl ether, tetraethylene glycol divinyl ether, and polytetahydrofuryl divinyl ether; trivinyl ether monomers such as trimethylolpropane trivinyl ether; tetafunctional vinyl ether monomers such as pentaerythritol tetravinyl ether; and mixture thereof. In certain embodiments, the polyvinyl ether monomer can further comprise one or more pendent groups selected from alkylene groups, hydroxyl groups, alkeneoxy groups, and amine groups.

Polythiols having the structure of Formula II may be prepared by reacting compounds having olefinic groups, such as vinylcyclohexene.

In certain embodiments, polyvinyl ethers in which R$^5$ is a C$_{2-6}$ branched alkylene can be prepared by reacting a polyhydroxy compound with acetylene. Exemplary compounds of this type comprise compounds in which R$^5$ is an alkyl-substituted methylene group such as —CH(CH$_3$)—, for example, PLURIOL® blends such as PLURIOL® E-200 divinyl ether (BASF Corp.) for which R$^5$=ethylene and m=3.8, or an alkyl-substituted ethylene, such as —CH$_2$CH(CH$_3$)—, for example, DPE® polymeric blends including DPE®-2 and DPE®-3 (International Specialty Products).

The reaction between a dithiol and a polyvinyl ether to prepare a polythiol having the structure of Formula II is described in U.S. Pat. No. 5,912,319.

The reaction between a dithiol and a polyvinyl ether to prepare a polythiol having the structure of Formula II may take place in the presence of a catalyst. The catalyst may be a free-radical catalyst, an ionic catalyst, or ultraviolet radiation. Preferably, the catalyst does not comprise acidic or basic compounds, and does not produce acidic or basic compounds upon decomposition. Examples of free-radical catalysts are an azo-type catalyst, including Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts are alkyl peroxides, such as t-butyl peroxide.

R$^2$ is a divalent linking group. In certain embodiments, R$^2$ may be derived from a monoepoxide having the structure of Formula III:

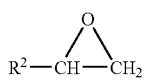

III in which $R^2$ includes groups that are reactive with sulfides such as, for example, olefinic groups. The olefinic group may be an alkylene group or an oxyalkylene group having from 3 to 20 carbon atoms and preferably from 3 to 5 carbon atoms. In certain embodiments, the monoepoxides having the structure of Formula III include allyl glycidyl ether, 1,2-epoxy-5-hexene, 1,2-epoxy-7-octene, 1,2-epoxy-9-decene, 4-vinyl-1-cyclohexene 1,2-epoxide, butadiene monoepoxide, isoprene monoepoxide, and limonene monoepoxide.

Consistent with the invention, another embodiment provides epoxy-capped polythioethers having the structure of Formula V:

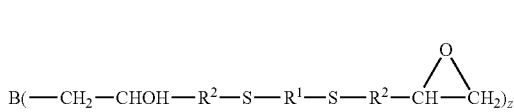

V where $R^1$ and $R^2$ are as described above, B is a multivalent radical, and z is a number corresponding to the valence of B.

B is a z-valent group and is derived from a compound, B', that represents a polyfunctionalizing agent. A polyfunctionalizing agent refers to a compound having more than two moieties that are reactive with epoxy groups. In certain embodiments, the polyfunctionalizing agent comprises from 3 to 6 such reactive moieties. Typically, B is denoted as a "z-valent" polyfunctionalizing agent, where z is the number of reactive moieties, and hence the number of separate branches comprising the polyfunctional epoxy-capped polythioether.

In certain embodiments of epoxy-capped polythioethers having the structure of Formula V, the polyfunctionalizing agent is a trifunctionalizing agent wherein z=3. In certain embodiments of a material of Formula V, the functional groups of the polyfunctionalizing agent are selected from acid groups, amine groups, anhydride groups, and thiol groups. Polyfunctionalizing agents having mixed functionality can also be used. Examples of polyfunctionalizing agents include tricarboxylic acids such as trimellitic acid and tricarballylic acid; polythiols such as described in U.S. Pat. No. 4,366,307, U.S. Pat. No. 4,609,762, and U.S. Pat. No. 5,225,472; and, triamines such as diethylene triamine and triethylene tetraamine.

Mixtures of polyfunctionalizing agents having a range of functionalities may also be used in the preparation of epoxy-capped polythioethers having the structure of Formula V. In certain embodiments, the use of certain amounts of trifunctionalizing agents affords epoxy-capped polythioethers having average functionalities from 2.05 to 3.0. Other average functionalities can be achieved by using tetrafunctional polyfunctionalizing agents, or polyfunctionalizing agents with higher valencies. The average functionality of the resulting epoxy-capped polythioether will also be affected by factors such as stoichiometry, as is known to those skilled in the art.

The difunctional epoxy-capped polythioethers of the invention having the structure of Formula I can be formed by the reaction of n moles of a dithiol having the structure of Formula II with n+1 moles of a monoepoxide having the structure of Formula III. The dithiol and monoepoxide may be reacted at a temperature of from about 40° C. to about 100° C., and typically from about 60° C. to 80° C. The dithiol and monoepoxide may be reacted for from about 10 hours to about 36 hours, and typically from about 12 hours to 24 hours. The dithiol may be any compound, polymer, or monomer having at least two thiol groups, and includes any of the exemplary polythiol compounds previously described. In certain embodiments, the monoepoxide having the structure of Formula II comprises one epoxy group and one olefinic group. The monoepoxide may be any of the exemplary monoepoxides previously described.

Optionally, the reaction occurs in the presence of a catalyst. Examples include free-radical catalysts, ionic catalysts, and ultraviolet light. In certain embodiments, the catalyst does not comprise an acidic or basic compound, and does not produce acidic or basic compounds upon decomposition. Preferably, the catalyst may be a free-radical catalyst, such as those described above.

Consistent with another embodiment of the invention, polyfunctional epoxy-capped polythioethers having the structure of Formula V can be formed by reacting at least one polythiol, at least one polyepoxide, and at least one polyfunctionalizing agent in appropriate stoichiometric amounts. Examples of polythiols, polyepoxides, and polyfunctionalizing agents include those as described above. Optionally, the reaction occurs in the presence of a catalyst as described above.

The epoxy-capped polythioethers described above can be combined with curing agents to form curable compositions. The epoxy-capped polythioethers described above can also be combined with other resins and curing agents to form curable compositions. In certain embodiments, curable compositions of the invention include from 0.2% to 10% by weight of at least one epoxy-capped polythioether as described above, at least one curing agent, and at least one resin where the weight percent is based on the total weight of the curable composition.

The term curing agent refers to a material that reacts with the epoxy group of the epoxy-capped polythioethers to form crosslinks. Examples of curing agents include polyacid curing agents, polyamine curing agents, polyanhydride curing agents, and polythiol curing agents. A polyacid curing agent refers to a compound having two or more acid groups per molecule which are reactive with the epoxy-capped polythioether to form a crosslinked composition. The acid functionality can be a carboxylic acid, or a sulfonic acid. Preferably, the polyacid curing agent may be a carboxyl-terminated compound having at least two carboxyl groups per molecule. Examples of polyacid curing agents include carboxylic acid group-containing polymers such as acrylic polymers, polyesters, and polyurethanes; and oligomers such as ester group-containing oligomers and monomers.

Examples of carboxylic acid-containing acrylic polymers are copolymers of (a) an ethylenically unsaturated monomer containing at least one carboxylic acid, and (b) a different ethylenically unsaturated monomer that is free from carboxylic acid groups. In certain embodiments, the amounts of monomer (a) and monomer (b) are selected such that the acid number of the polyacid acrylic polymer is from 30 to 150, preferably from 60 to 120. Examples of carboxylic acid-containing acrylic monomers are acrylic acid, methacrylic acid, maleic acid, and partial esters of maleic acid. The other monomeric component (b) is characterized by the group,

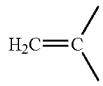

and may be styrene, an alpha-substituted lower alkyl styrene such as alpha-methylstyrene, an alkyl ester of acrylic and methacrylic acid, such as methyl methacrylate, methyl acrylate, and ethyl acrylate, and mixtures of these materials.

In other embodiments, the polyacid curing agent may be a monomeric polycarboxylic acid having from 5 to 20 carbon atoms including open chain, cyclic, saturated, unsaturated, and aromatic acids. Examples of suitable monomeric polycarboxylic acids include succinic acid, adipic acid, azelaic acid, sebacic acid, hexahydrophthalic acid, maleic acid, cyclohexene-1,2-dicarboxylic acid, and phthalic acid.

Polyamine curing agent including primary and secondary diamines or polyamines in which the radicals attached to the nitrogen atoms can be saturated or unsaturated, aliphatic, alicyclic, aromatic, aromatic-substituted aliphatic, aliphatic-substituted aromatic, or heterocyclic. In other embodiments, the polyamine curing agent may include mixed amines in which the radicals are different such as, for example, aromatic groups, aliphatic groups, and other non-reactive groups attached to the carbon atoms such as oxygen, sulfur, halogen, or nitro groups. Examples of suitable aliphatic and alicyclic diamines include 1,2-ethylene diamine, 1,2-propylene diamine, 1,8-p-menthane diamine, isophorone diamine, propane-2,2-cyclohexyl amine, and methane-bis-(4-cyclohexyl amine), and

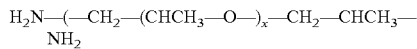

where x is from 1 to 10.

The polyamine curing agent includes phenylene diamines and toluene diamines such as, for example, o-phenylene diamine and p-tolylene diamine, and N-alkyl and N-aryl derivatives thereof such as, for example, N,N'-dimethyl-o-phenylene diamine, N,N'-di-p-tolyl-m-phenylene diamine, and p-amino-diphenylamine.

The polyamine curing agent may be a polynuclear aromatic diamine in which the aromatic rings are attached by means of a valence bond such as, for example, 4,4'-biphenyl diamine, methylene dianiline, and monochloromethylene dianiline.

Epoxy-capped polythioethers of the invention mar be used in curable compositions, such as sealants, coatings, and adhesives, either alone or in combination with other resins. In certain embodiments, curable compositions of the invention may include fillers and additives as appropriate for specific applications.

Fillers may be added to curable compositions of the invention to impart desirable physical properties such as, for example, to increase the impact strength, to control the viscosity, to modify the electrical properties, or to reduce the specific gravity. Fillers useful in the curable compositions of the invention for aviation and aerospace applications include those commonly used in the art, such as carbon black, calcium carbonate, silica, and polymer powders. Exemplary fillers include Sipernat® D-13 hydrophobic precipitated silica (Degussa), Winnofil® SPM precipitated calcium carbonate (Solvay Chemicals), TS-270 (Cabot Corporation), titanium dioxide (DuPont), aluminum hydroxide, and Orgasol® 1002 D Nat 1 ultrafine polyamide powder (Atofina Chemicals). In certain embodiments, the filler comprises from 5% by weight to 60% by weight of the non-volatile components of the curable composition.

The curable compositions of the invention usually comprise at least one additive selected from the following: plasticizers, pigments, cure accelerators, adhesion promoters, thixotropic agents, fire retardants, masking agents, antioxidants, and surfactants. The additive may be present in the curable composition in amounts of 0.1 to 40% by weight based on the total weight of the curable composition.

The plasticizer may include at least one of the following: phthalate esters, chlorinated paraffins, and hydrogenated terphenyls. Examples of useful plasticizers include HB-40® modified polyphenyl (Solutia, Inc.) and tung oil (Campbell & Co.). In certain embodiments, the plasticizer comprises from 1% by weight to 40% by weight of the total weight of the curable composition, more typically from 1% by weight to 8% by weight of the total weight of the curable composition.

The curable compositions of the invention may comprise at least one pigment. Examples of pigment include at least one of the following: carbon black, metal oxides, and calcium carbonate. Pigment grade carbon black generally is characterized by low structure and particle size such as Regal® 660R (Cabot Corporation). Brilliant 1500 is an example of pigment grade, 99.995$^+$%, calcium carbonate (Aldrich Chemical). In certain embodiments, the pigment comprises from 0.1% by weight to 10% by weight of the total weight of the curable composition. In other embodiments, the pigment comprises from 0.1% by weight to 5% by weight of the total weight of the curable composition.

Curable compositions of the invention are cured according to recommended procedures and, in certain embodiments, at ambient temperature. "Curable" refers to the capability of undergoing one or more chemical reactions to form stable, covalent bonds among the constituent components. The curable compositions are usually curable at a minimum temperature of 50° C. to 100° C. and more typically from 60° C. to 75° C.

EXAMPLES

Reference will now be made in detail to specific embodiments of the invention. While certain embodiments of the invention will be described in conjunction with the preferred embodiments, it will be understood that it is not intended to limit the embodiment of the invention to those preferred embodiments. To the contrary, it is intended to cover alternatives, modifications, and equivalents as may be included within the spirit and scope of the embodiments of the invention as defined by the appended claims.

The following tests were used to characterize certain curable compositions of the invention:

Chemical resistance was determined according to ASTM D 1308, 24 Hour Spot Test.

Hardness was determined according to MMS 332 4.4.18 and AMS 3277 4.5.5.

Viscosity was determined according to MMS 332 4.4.4 and AMS 3277 4.5.8.

Odor was determined empirically.

Color was determined according to Gardner method.

Epoxy equivalent weight was determined according to ASTM 1652.

Tensile strength was determined according to ASTM D 412.

Elongation was determined according to ASTM D 412.

Example 1

253.4 g (1.39 mole) of dimercaptodioxaoctane (DMDO) was added to a 1 liter 4-neck flask under a nitrogen atmosphere. While stirring, the contents of the flask was heated to 50° C., and 146.6 g (0.93 mole) of diethylene glycol divinyl ether (DEG-DVE) was added over 1 hr. The temperature of the reaction mixture was increased to 70° C. and 0.05 g of free-radical initiator Vazo® 67 (2,2'-azobis(2-methylbutyronitrile), Du Pont) was added. The temperature of the reaction mixture was maintained at 70° C. for an additional hour. Completion of the reaction of DEG-DVE with DMDO was indicated by a mercaptan equivalent value of 420. Allyl glycidyl ether (AGE) (110.87 g, 0.97 mole, 2% stoichiometric excess) was added at 70° C. over 1 hr and the reaction mixture was heated at 70° C. for an additional hour. Ten portions of Vazo®67 (0.165 g each) were then added at 3 hr intervals at 70° C. Following addition of Vazo® 67 the reaction mixture was heated at 70° C. for 5 hr. The reaction mixture was then degassed at 70° C./4-5 mm Hg for 3 hr to provide a liquid epoxy-capped polythioether having a faint yellow color, a viscosity of 5.0 poise, and an epoxy equivalent value of 563. The reaction yield was 508.7 g (100%).

Example 2

62.17 g (moles) of DMDO was added to a 250 ml 3-neck flask under a nitrogen atmosphere. While stirring, DMDO was heated to 60° C. and 44.88 g (mole) of DEG-DVE was added to the reaction mixture over a period of 50 minutes while the temperature of the reaction was maintained at 60° C.-70° C. The reaction mixture was heated at 70° C. for an additional 4 hr. Two portions of Vazo® 67 (0.036 g each) were added to the reaction mixture at 1.5 hr intervals and heated at 70° C. for 1.5 hr. The mercaptan equivalent value of the reaction mixture was 890. An additional portion of Vazo® 67 (0.036 g) was added and the reaction mixture heated for another 1.5 hr. A mercaptan equivalent value of 893 indicated completion of the reaction of DEG-DVE with DMDO. AGE (13.21 g, 0.116 mole, 2% stoichiometric excess) was added at 70° in one portion and the reaction mixture was heated for 2 hr. Eight portions of Vazo® 67 (0.035 g each) were added at 3 hr intervals at 70° C. and heating was continued for another 4 hr. At this stage, the mercaptan equivalent value of the reaction mixture was of 28,642. To complete the reaction, an additional 4.8 g (0.042 mole, 38% stoichiometric excess) of AGE was added and the reaction mixture was heated for 1 hr at 70° C. Two portions of Vazo® 67 (0.036 g each) were added at 3 hr intervals. Following the addition of Vazo® 67, the reaction mixture was heated at 70° C. for 5 hours. The reaction mixture was then degassed at 70° C./4-5 mm Hg for 2 hr to provide a slightly hazy, liquid epoxy-capped polythioether having a faint yellow color, a viscosity of 26 poise, and an epoxy equivalent value of 1,217. The reaction yield was 120.0 g (100%).

Curable Composition 1 was prepared by combining 12.5 parts by weight of the epoxy-capped polythioether of Example 1, 37.5 parts by weight of Epon 828, 28 to 29 parts by weight of Epi-Cure 3155, and 0.5 parts by weight of DMP 30. Curable composition 1 was cured at a temperature of 689° F. for one week. A summary of the properties of cured Composition 1 is presented in Table 1.

TABLE 1

Properties of Cured Composition 1.

| Property | Composition 1 |
| --- | --- |
| Physical state | Clear amber Liquid |
| Odor | none |
| Color | 3 max |
| Viscosity at 25° C. (poise) | 5 |
| Specific Gravity | 1.13 |
| Epoxy Equivalent Value | 530-650 |
| Tg, DSC (° C.) | −42.0 ± 1.0 |
| Gel Time (minutes) | 196 |
| Compatibility with epoxy/ECA | Good |
| HYC | none |
| Chemical Resistance: (24 Hour Spot Test) | |
| 10% $H_2SO_4$ | Excellent |
| 10% Acetic Acid | Excellent |
| 10% HCl | Excellent |
| 2% $HNO_3$ | Some Yellowing |
| 10% NaOH | Excellent |
| Skydrol | Excellent |
| Xylene | Excellent |
| Hardness, pencil | 2H |
| Tensile Strength | 1125 pli |
| Elongation | 2.07% |

When cured, curable Composition 1 exhibits excellent chemical resistance, including excellent resistance to aviation and aerospace fuels.

The viscosity of curable Composition 1 of 5 poise at a temperature of 25° C. is six times less than epoxy-terminated polysulfides produced using epichlorohydrin. The low viscosity of the epoxy-capped polythioethers of the invention provide greater latitude in producing formulations than comparable compositions prepared with epoxy-terminated polysulfides produced using epichlorohydrin. Other desirable attributes include a low specific gravity of 1.13, a low epoxy equivalent weight of from 530 to 650, and the epoxy-capped polythioethers are compatible with amines and other epoxy compounds.

What is claimed is:

1. An epoxy-capped polythioether comprising:
   a reaction product of n moles (i) a dithiol and divinyl ether reaction product; and n+1 moles (ii) a monoepoxy olefin, wherein the dithiol and divinyl ether reaction product was formed by reacting n+1 moles of a dithiol having a structure HS—$R^1$—SH and n moles of a divinyl ether having a structure $CH_2$=CH—O—[—$R^5$—O—]$_m$—CH=$CH_2$,
   wherein $R^1$ and $R^5$ are each independently selected from the group consisting of $C_{2-6}$ n-alkylene, $C_{3-6}$ branched alkylene, $C_{6-8}$ cycloalkylene, $C_{6-10}$ alkylcycloalkylene, and —[—$(CHR^3)_p$—X—]$_q$—$(CHR^3)_r$—, wherein
   each $R^3$ is independently selected from H, and —$CH_3$,
   each X is independently selected from O, S, —NH—, and —$NR^4$—,
   $R^4$ is selected from H, and —$CH_3$,
   p is an integer from 2 to 6,
   q is an integer from 1 to 5,
   r is an integer from 2 to 10, and
   m is an integer from 1 to 10.

2. The epoxy-capped polythioether of claim 1, wherein the dithiol is selected from the group consisting of dimercaptodioxaoctane, and dimercaptodiethylsulfide.

3. The epoxy-capped polythioether of claim 1, wherein the divinyl ether is selected from the group consisting of an alkylene having from 3 to 5 carbon atoms, and an oxyalkylene having from 3 to 5 carbon atoms.

4. The epoxy-capped polythioether of claim 1, wherein the divinyl ether comprises at least one alkylene oxy group.

5. The epoxy-capped polythioether of claim 1, wherein the monoepoxy olefin has a structure

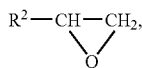

wherein $R^2$ is an olefinic group.

6. The epoxy-capped polythioether of claim 1, which is free of hydrolizable chlorine.

7. The epoxy-capped polythioether of claim 1, having an epoxy-equivalent weight range less than 300.

8. A method for making the epoxy-capped polythioether of claim 1, comprising:
reacting n moles (i) a dithiol and divinyl ether reaction product; with n+1 (ii) a monoepoxy olefin, wherein the dithiol and divinyl ether reaction product was formed by reacting n+1 moles of a dithiol having a structure HS—$R^1$—SH and n moles of a divinyl ether having a structure $CH_2$=CH—O—[—$R^5$—O—]$_m$—CH=$CH_2$, wherein $R^1$ and $R^1$ are each independently selected from the group consisting of $C_{2-6}$ n-alkylene, $C_{3-6}$ branched alkylene, $C_{6-8}$ cycloalkylene, $C_{6-10}$ alkylcycloalkylene, and —[—($CHR^3$)$_p$—X—]$_q$—($CHR^3$)$_r$—, wherein each $R^3$ is independently selected from H, and —$CH_3$, each X is independently selected from O, S, —NH—, and —$NR^4$—,
$R^1$ is selected from H, and —$CH_3$, p is an integer from 2 to 6,
q is an integer from 1 to 5,
r is an integer from 2 to 10, and
m is an integer from 1 to 10.

9. The method of claim 8, wherein the dithiol and divinyl ether reaction product is formed in the presence of a catalyst selected from the group consisting of a free radical catalyst, and ultraviolet light.

10. The method of claim 8, wherein the catalyst does not comprise an acidic or basic compound and does not produce acidic or basic compounds upon decomposition.

11. The method of claim 8, wherein the catalyst comprises a free radical catalyst.

12. The method of claim 11, wherein the free radical catalyst is selected from the group consisting of azo catalysts, and alkyl peroxides.

13. The method of claim 12, wherein the azo catalyst is an azobis(isobutyronitrile) catalyst.

14. The epoxy-capped polymer of claim 1, wherein the divinyl ether is diethylene glycol divinyl ether.

15. The epoxy-capped polymer of claim 5, wherein the monoepoxy olefin is selected from the group consisting of allyl glycidyl ether, 1,2-epoxy-5-hexene, 1,2-epoxy-7-octene, 1,2-epoxy-9-decene, 4-vinyl-1-cyclohexene 1,2-epoxide, butadiene monoepoxide, isoprene monoepoxide, and limonene monoepoxide.

16. The epoxy-capped polymer of claim 2, wherein the dithiol comprises dimercaptodioxaoctane.

17. The epoxy-capped polymer of claim 15, wherein the monoepoxy olefin comprises allyl glycidyl ether.

* * * * *